United States Patent
Das

(10) Patent No.: US 7,264,807 B2
(45) Date of Patent: Sep. 4, 2007

(54) TREATMENT OF ULCERATIVE COLITIS WITH TROPOMYOSIN ISOFORMS AND MONOCLONAL ANTIBODIES TO TROPOMYOSIN ISOFORMS

(75) Inventor: Kiron M. Das, Basking Ridge, NJ (US)

(73) Assignee: University of Medicine and Dentistry of New Jersey, New Brunswick, NJ (US)

( * ) Notice: Subject to any disclaimer, the term of this patent is extended or adjusted under 35 U.S.C. 154(b) by 137 days.

(21) Appl. No.: 10/427,196

(22) Filed: May 1, 2003

(65) Prior Publication Data

US 2003/0198635 A1 Oct. 23, 2003
US 2007/0025984 A9 Feb. 1, 2007

Related U.S. Application Data

(63) Continuation of application No. 09/046,049, filed on Mar. 23, 1998, now Pat. No. 6,605,276, which is a continuation-in-part of application No. 08/630,541, filed on Apr. 10, 1996, now Pat. No. 5,869,048, which is a continuation-in-part of application No. 08/437,474, filed on May 9, 1995, now abandoned.

(51) Int. Cl.
*A61K 39/395* (2006.01)
(52) U.S. Cl. .............................. 424/152.1; 424/139.1; 424/156.1; 530/388.1; 530/387.9
(58) Field of Classification Search .............. 424/133.1, 424/139.1, 141.1
See application file for complete search history.

(56) References Cited

U.S. PATENT DOCUMENTS 5,783,193 A 7/1998 Michael et al.
6,605,276 B1 8/2003 Das

FOREIGN PATENT DOCUMENTS

WO WO96/35449 9/1996

OTHER PUBLICATIONS

Warren et al., J. Cell. Biol., 1995, 129:697-708.*
Lin et al., J. Cell. Biol., 1988, 107:563-572.*
Halstensen et al., Adv Exp Med Biol 1995, 371B:1273-1276.*
Halstensen et al., Gut, 1993, 34:650-657.*
Gelderman et al., Trends in Immunology, 2004, 25:158-164.*
Geng et al., Gastroenterology, 1998, 114:912-922.*
Lab Vision Product Data Sheet for "Tropomyosin Ab-3 (Clone CG1)".
Dunn et al. (2003) Altered Tropomyosin Expressin in Essential Hypertension. Hypertension 41:347-354.

* cited by examiner

*Primary Examiner*—G. R. Ewoldt
*Assistant Examiner*—Michael Szperka
(74) *Attorney, Agent, or Firm*—Licata & Tyrrell P.C.

(57) ABSTRACT

This invention pertains to a method for treating ulcerative colitis. Specifically, the method comprises orally or rectally administering to a human having ulcerative colitis a therapeutically effective amount of an antibody which binds to a tropomyosin isoform associated with ulcerative colitis. In another embodiment, the invention pertains to a method for treating ulcerative colitis in a human which comprises the steps of (a) obtaining from a human a colon epithelial cell extract containing a tropomyosin isoform associated with ulcerative colitis; (b) purifying the tropomyosin isoform until the tropomyosin isoform is substantially homogeneous; (c) developing an antibody which binds to the tropomyosin isoform; and (d) orally or rectally administering to a human having ulcerative colitis a therapeutically effective amount of the antibody to bind to the tropomyosin isoform associated with ulcerative colitis. In yet another embodiment, the invention pertains to a method for treating ulcerative colitis in a human which comprises orally administering to the human a therapeutically effective amount of a tropomyosin isoform associated with ulcerative colitis.

3 Claims, 4 Drawing Sheets

TREATMENT OF ULCERATIVE COLITIS WITH TROPOMYOSIN ISOFORMS AND MONOCLONAL ANTIBODIES TO TROPOMYOSIN ISOFORMS

This Application is a Continuation of U.S. Pat. application Ser. No. 09/046,049 filed Mar. 23, 1998, now U.S. Pat. No. 6,605,276, which is a continuation-in-part of U.S. Pat. application Ser. No. 08/630,541, filed Apr. 10, 1996, now U.S. Pat. No. 5,869,048, which is a continuation-in-part of U.S. Pat. application Ser. No. 08/437,474, filed May 9, 1995, now abandoned. Priority to these applications is claimed under 35 U.S.C. § 120.

STATEMENT OF RIGHTS TO INVENTIONS MADE UNDER FEDERALLY-SPONSORED RESEARCH AND DEVELOPMENT

Part of the work performed during development of this invention utilized United States Government funds. The United States Government has certain rights in this invention: NIADDK RO1 DK47673 from the National Institutes of Health (Bethesda, Md.).

BACKGROUND OF THE INVENTION

1. Field of the Invention

This invention pertains to a method for treating ulcerative colitis. Specifically, the method comprises orally or rectally administering to a human having ulcerative colitis a therapeutically effective amount of an antibody which binds to a tropomyosin isoform associated with ulcerative colitis. In another embodiment, the invention pertains to a method for treating ulcerative colitis in a human which comprises the steps of (a) obtaining from a human a colon epithelial cell extract containing a tropomyosin isoform associated with ulcerative colitis; (b) purifying the tropomyosin isoform until the tropomyosin isoform is substantially homogeneous; (c) developing an antibody which binds to the tropomyosin isoform; and (d) orally or rectally administering to a human having ulcerative colitis a therapeutically effective amount of the antibody to bind to the tropomyosin isoform associated with ulcerative colitis. In yet another embodiment, the invention pertains to a method for treating ulcerative colitis in a human which comprises orally administering to the human a therapeutically effective amount of a tropomyosin isoform associated with ulcerative colitis.

2. Description of the Background

The disclosures referred to herein to illustrate the background of the invention and to provide additional detail with respect to its practice are incorporated herein by reference and, for convenience, are numerically referenced in the following text and respectively grouped in the appended bibliography.

Ulcerative colitis (UC) is a chronic inflammatory bowel disease (IBD) of unknown etiology, although autoimmunity has been emphasized in the pathogenesis of the disease (1). A marked increase in the mucosal IgG immunocytes (2) and IgG antibodies against colonic antigens (3) and neutrophil antigen (4) have been reported in ulcerative colitis colon. However, the specific antigen(s) involved in the IgG-immune recognition has not been clarified. The mucosal IgG overproduction could play pathogenetic role in ulcerative colitis as the subclass distribution of IgG-producing cells in both active and inactive ulcerative colitis lesions shows a disproportionate local overproduction of IgG1 (5,6). IgG1 antibodies are more effective in complement activation than IgG2 (7) and because of this property, IgG1 antibodies can contribute to the perpetuation of tissue damage in ulcerative colitis.

The presence of tissue-bound IgG antibody in the ulcerative colitis colon has been reported (8) and it was demonstrated that this IgG antibody recognized an Mr 40K colonic protein, (p40) (9). Tissue-bound IgG eluted from Crohn's disease of the colon (CD) and controls did not recognize the p40, suggesting an autoantigenic role of this protein in ulcerative colitis (9). By immunocytochemical methods, other investigators reported the deposition of IgG1 autoantibody and activated complement products on the colonic epithelium from active ulcerative colitis (10,11), but not in Crohn's colitis (12). Recently, p40 was purified from the colon to homogeneity, partially sequenced, and the two peptides derived therefrom showed 93-100% identity with the cytoskeletal protein tropomyosins (TMs) (13). Tropomyosins are cytoskeletal microtubular proteins present in all eukaryotic cells with organ specific isoforms, and multiple isoforms may be present in the same cell (14). At least 8 tropomyosin isoforms have been identified from human fibroblast cells (15) and strong evidence for the distinct functions performed by different tropomyosin isoforms has recently been generated (14). Tropomyosins are capable of inducing significant immune responses related to allergy (16) as well as autoimmunity (17). In a computer-based physico-chemical analysis, several sequences of tropomyosin-residues were considered to be among the most potent autoantigens (17). It has been reported that blood serum from patients with ulcerative colitis, but not from Crohn's colitis and other controls, had IgG antibodies reactive to tropomyosins (13). The specific tropomyosin isoform(s) present in the human colon epithelium is unknown.

SUMMARY OF THE INVENTION

Figure 1:
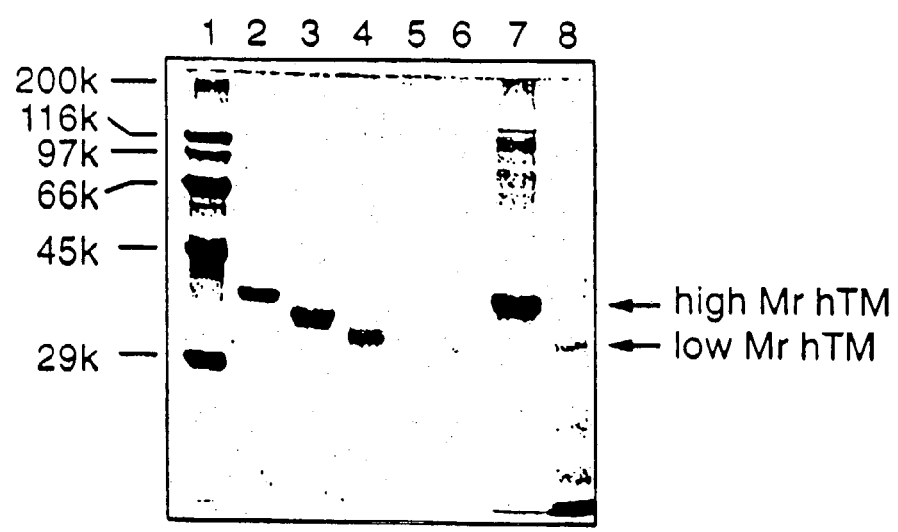
FIG. 1 illustrates an SDS-polyacrylamide gel electrophoresis followed by Coomassie blue staining of purified recombinant human tropomyosin isoforms (hTM1-5) and enriched hTMs from colon epithelial cells and colon smooth muscle.

The present invention pertains to a method for treating ulcerative colitis in a human which comprises orally or rectally administering to the human a therapeutically effective amount of an antibody which binds to a tropomyosin isoform associated with ulcerative colitis.

In another embodiment, the present invention pertains to a method for treating ulcerative colitis in a human which comprises the steps of:

(a) obtaining from a human a colon epithelial cell extract containing a tropomyosin isoform associated with ulcerative colitis;

(b) purifying the tropomyosin isoform until the tropomyosin isoform is substantially homogeneous;

(c) developing an antibody which binds to the tropomyosin isoform; and (d) orally or rectally administering to a human having ulcerative colitis a therapeutically effective amount of the antibody to bind to the tropomyosin isoform associated with ulcerative colitis.

In one embodiment, the tropomyosin isoform is hTM1. In another embodiment, the tropomyosin isoform is hTM5. Preferably, the antibody is monoclonal antibody CG1 (IgG1) or monoclonal antibody CG3 (IgM). The antibody may be administered in an amount from about 50 µg/day to about 500 µg/day. Preferably, the antibody is administered rectally. The antibody may be a murine antibody.

In yet another embodiment, the present invention pertains to a method for treating ulcerative colitis in a human which comprises orally administering to the human a therapeutically effective amount of a tropomyosin isoform associated with ulcerative colitis. In one embodiment, the tropomyosin isoform is hTM1. In another embodiment, the tropomyosin isoform is hTM5. The tropomyosin isoform may be administered in an amount from about 50 µg/day to about 1000 µg/day.

DETAILED DESCRIPTION OF THE INVENTION

In accord with the present invention, the hTM isoforms (hTM1-5) present in intestinal epithelial cells and in smooth muscle, and the immunoreactivity against hTMs by IgG produced in vitro by colonic mucosal lymphocytes (LPMC) from patients with ulcerative colitis, Crohn's colitis (CD), and controls, were examined. Tropomyosins were extracted from colonic and jejunal epithelial cells and smooth muscle and the hTM isoforms were identified using isoform specific monoclonal antibodies by ELISA and transblot analysis. Immunoreactivity of IgG produced by colonic LPMC was analyzed against the recombinant hTM isoforms. This study showed that the major hTM isoforms present in colonic and jejunal epithelial cells are hTM5 and hTM4, whereas intestinal smooth muscle contains hTM 1-3 isoforms. The IgG synthesized in vitro by LPMCs from ulcerative colitis (n=19) had significantly (p<0.04<0.001) higher reactivity against hTM5 and hTM1, and not against hTM2 and hTM3, when compared to Crohn's colitis (n=12) and controls (n=17). However, IgG produced by LPMC from Crohn's colitis did not show such anti-hTM reactivity. Mucosal anti-hTM IgG mainly belonged to IgG1 subclass. Accordingly, it was found that intestinal epithelial cells and smooth muscle have distinct hTM isoforms, and patients with ulcerative colitis, and not Crohn's colitis, demonstrate mucosal autoantibody response against hTM isoforms, particularly hTM5 and hTM1.

In one embodiment, the present invention pertains to a method for treating ulcerative colitis in a human which comprises orally or rectally administering to the human a therapeutically effective amount of an antibody which binds to a tropomyosin isoform associated with ulcerative colitis.

The tropomyosin isoform associated with ulcerative colitis used in the present invention may be any tropomyosin isoform associated with ulcerative colitis. Preferably, the tropomyosin isoform is hTM1 or hTM5. More preferably, the tropomyosin isoform is hTM5.

The antibody which binds to a tropomyosin isoform associated with ulcerative colitis used in the present invention may be any antibody. Preferably, the antibody is a murine antibody or a humanized antibody. More preferably, the antibody is monoclonal antibody CG1 (IgG1), also referred to as LC1, or monoclonal antibody CG3 (IgM). Most preferably, the antibody is monoclonal antibody CG3 (IgM). Monoclonal antibodies CG1 and CG3 are described in more detail in Novy et al., Cell Motil Cytoskeleton 1993;26:248-261; Lin et al., J Cell Biol 1988;107:563-572; Warren et al., J Cell Biol 1995;129:697-708; Lin et al., International Review Cytology 1997;170:1-38; and Lin et al., Hybridoma 1985;4:223-242; which disclosures are incorporate herein by reference.

The amount of antibody which binds to a tropomyosin isoform associated with ulcerative colitis used in the present invention is a therapeutically effective amount. A therapeutically effective amount of antibody is that amount of antibody necessary to bind to a tropomyosin isoform associated with ulcerative colitis blocking the epithelial binding of circulating and/or local auto antibodies causing ulcerative colitis. The exact amount of antibody is a matter of preference subject to such factors as the type of condition being treated as well as the dosage recommended or permitted for the particular antibody. In general, the amount of antibody agent employed is the dosage required to obtain the desired result. In a preferred embodiment, the dosage of antibodies in an enema for patients with ulcerative colitis will be in the range from about 50 µg/day to about 500 µg/day, preferably from about 100 µg/day to about 400 µg/day, and more preferably from about 150 µg/day to about 300 µg/day. Most preferably, the dosage of antibodies will be about 100 µg in the form of a retention enema given once or twice a day for up to about 8 weeks.

The antibody may be administered orally or rectally. Preferably, the antibody is administered rectally.

The present invention extends to methods for preparing the antibodies which bind to a tropomyosin isoform associated with ulcerative colitis used in the present invention. The antibodies may be developed using standard techniques and apparatus known to those skilled in the art. In a preferred embodiment, the invention is directed to a method for treating ulcerative colitis in a human which comprises the steps of:

(a) obtaining from a human a colon epithelial cell extract containing a tropomyosin isoform associated with ulcerative colitis;

(b) purifying the tropomyosin isoform until the tropomyosin isoform is substantially homogeneous;

(c) developing an antibody which binds to the tropomyosin isoform; and (d) orally or rectally administering to a human having ulcerative colitis a therapeutically effective amount of the antibody to bind to the tropomyosin isoform associated with ulcerative colitis.

In another embodiment, the present invention is directed at a method for treating ulcerative colitis in a human through oral tolerance. Oral tolerance is the state of hyporesponsiveness that follows immunization with a previously fed protein. Animals fed antigenic proteins have been shown not to respond as well to these antigens when subsequently immunized but do respond normally to other antigens. Immunological tolerance is a fundamental property of the immune system that provides a mechanism for self/nonself discrimination. Through immunological tolerance, the immune system can protect the host from external pathogens (against nonself) without eliciting autoimmune disease (against self). Oral tolerance has been used to treat autoimmune diseases in animal models and is now being applied to the treatment of human diseases. As with immunological tolerance, oral tolerance has been found to involve multiple mechanisms and is not a single immunological event. The primary mechanisms by which oral tolerance is mediated include deletion, anergy, and active cellular suppression. The determining factor in this process is the dose of fed antigen. Low doses favor active suppression, high doses favor deletion and anergy. Oral tolerance is reviewed in detail in Weiner, H. L., Immunology Today, 19, 335-343 (1997), which disclosure is incorporated herein by reference. In this embodiment, a patient having ulcerative colitis is tolerized or desensitized by being treated with a tropomyosin isoform associated with ulcerative colitis in multiple doses over a period of time sufficient to develop tolerance in the patient. Developing tolerance in the patient causes the immune system to become non-reactive to the tissue-autoantigen.

In a specific embodiment, the present invention pertains to a method for treating ulcerative colitis in a human which comprises orally administering to the human a therapeutically effective amount of a tropomyosin isoform associated with ulcerative colitis.

The tropomyosin isoform associated with ulcerative colitis used in this method may be any tropomyosin isoform, or an antigenically active fragment thereof, associated with ulcerative colitis. Preferably, the tropomyosin isoform is hTM1 or hTM5. More preferably, the tropomyosin isoform is hTM5.

The amount of tropomyosin isoform associated with ulcerative colitis used in this method is a therapeutically effective amount. A therapeutically effective amount of tropomyosin isoform is that amount of tropomyosin isoform necessary to develop tolerance in the patient causing the immune system to become non-reactive to the tropomyosin isoform associated with ulcerative colitis. The exact amount of tropomyosin isoform is a matter of preference subject to such factors as the type of condition being treated as well as the dosage recommended or permitted for the particular tropomyosin isoform. In general, the amount of tropomyosin isoform employed is the dosage required to obtain the desired result. In a preferred embodiment, the dosage of tropomyosin isoform for patients with ulcerative colitis will be in the range from about 50 μg/day to about 1000 μg/day, preferably from about 100 μg/day to about 750 μg/day, and more preferably from about 150 μg/day to about 500 μg/day. Most preferably, the dosage of tropomyosin isoform will be about 100 μg in given orally once or twice a day for up to about 8 weeks.

The present invention is further illustrated by the following examples which are not intended to limit the effective scope of the claims. All parts and percentages in the examples and throughout the specification and claims are by weight of the final composition unless otherwise specified.

EXAMPLES

Extraction of Tropomyosin from the Intestinal Tissue

Colonic and Small Intestinal Mucosal Extracts Enriched in Tropomyosins

Colonic mucosa (including epithelium and stromal tissue and muscularis mucosa) was stripped from operative specimens of colon from patients with colon cancer (normal segments, n=4). Jejunal mucosa was obtained from normal subjects (n=4) who underwent gastric by-pass surgery for morbid obesity. Mucosa was minced, washed with phosphate buffered saline (PBS), re-suspended in the buffer containing 1 M NaCl, 50 mM Tris, 1 mM EDTA, 5 mM DTT, and 2 mM PMSF, and ultrasonicated for 3 minutes on ice. The sample was centrifuged at 1,000 g for 5 minutes, the supernatant boiled for 10 minutes, centrifuged at 7,000 rpm for 30 minutes, and further purified by ammonium sulfate precipitation (initially 40% and then 60%) (15) and stored until use.

Extraction of Tropomyosins from Colonic and Jejunal Epithelial Cells

Stripped mucosa from the surgical specimens was washed with Hank's balanced salt solution (HBSS) containing gentamycin 50 units/ml, 100 U of penicillin and 100 mg of streptomycin. To remove the mucus, the tissue was treated with 1 mM DTT for 15 min at 37° C. followed by 3 washings in HBSS. The tissue was subjected to dispase treatment 3 mg/ml in RPMI 1640 for 30 min at 37° C. Cells were collected from supernatant and epithelial cells were further purified by Percoll (Pharmacia, N.J.) gradient (44% and 66%), and centrifugation at 1000 g for 30 min. The top layer was transferred, washed with PBS and the cells were counted and stored at −80° C. until further extraction. The purity of epithelial cells was found to be at least 90%. Tropomyosins were extracted by homogenization of the cell pellet in the buffer containing 0.35M NaCl, 50 mM Tris, 1 mM EDTA, 5 mM DTT and 2 mM PMSF, centrifuged at 1,000 g for 5 minutes and the supernatant boiled for 10 minutes, followed by centrifugation at 7000 rpm for 30 minutes. The supernatant was further purified by sequential ammonium sulfate precipitation.

Extraction of Tropomyosins from Colonic and Small Intestinal Smooth Muscle

Smooth muscle was dissected from the intestinal specimens after stripping off the mucosa, and tropomyosins were extracted, as described above.

Preparation of Recombinant Tropomyosin Isoforms

The full-length cDNAs encoding various tropomyosin isoforms (hTM1, hTM2, hTM3 and hTM5) were prepared from human fibroblast, as reported earlier (15). hTM4 clone was not available. We have subcloned these 4 cDNA clones into prokaryotic expression vector pET8c. The resulting plasmids were transformed into E coli BL21 (D3) LysS strain. Recombinant human tropomyosin isoforms were purified from bacterial lysates by ammonium sulfate fractionation, DE-52 ion-exchange chromatography, and hydroxyapatite column chromatography. The purity of the hTM isoforms was examined by SDS polyacrylamide gel electrophoresis (SDS-PAGE) and the immunoreactivity was analyzed by ELISA and transblot analysis using isoform specific monoclonal antibodies.

Monoclonal Antibodies Against Various Tropomyosin Isoforms

The isoform specific murine monoclonal antibodies CG1 (IgG1) against hTM1, CGb6 (IgM) against hTM2/hTM3, and CG3 (IgM) against hTM5 were generated and characterized earlier (14,15). CGb6 reacts with both hTM2 and hTM3 but not against hTM1, hTM4 or hTM5. The isoform-specific monoclonal antibodies LC24 (IgG1) against hTM4 and LC1 (IgG1) against hTM5 were generated by immunizing mice with the recombinant hTM isoform (18).

Determination of Specific Tropomyosin Isoform(s) in the Colon and Small Intestine by Immunotransblot Analysis and by Elisa Extracted tropomyosins from mucosa, isolated epithelial cells and smooth muscle from the small and large intestine were examined by SDS-PAGE followed by immunotransblot analysis (9). Five ug of enriched tropomyosin extracts were separated by 12% SDS-PAGE, stained with Coomassie brilliant blue. Separated proteins were also transferred to nitro-cellulose sheet blocked with 1% bovine serum albumin (BSA) and probed with isoform specific murine anti-tropomyosin monoclonal antibodies (CG1—1:1,000, CG3—1:500, CGb6—1:1,000, LC1—1:500, LC24—1:500), followed by horseradish peroxidase conjugated appropriate anti-mouse IgM or IgG antibodies. The reactivity was detected by chemiluminescence using Renaissance Kit (Dupont, Boston, Mass.), and respective recombinant hTM isoform (2 ug) was run in parallel as positive control. Unrelated isotype specific murine monoclonal antibodies such as MOPC-IgM or MOPC-IgG were also used to examine any non-specific reactivity.

Tropomyosin extracts from jejunal and colonic mucosa, smooth muscle, and small intestinal enterocytes and colonocytes were also analyzed by ELISA. The extracts were plated (0.3 ug/well) in carbonate buffer (pH 9.6) on ELISA plate for overnight. The tropomyosin isoform specific monoclonal antibodies, as described above, were incubated at 37° C. for 1 hour after blocking the plate with 1% normal goat serum, followed by alkaline phosphatase conjugated appropriate (anti-mouse IgM or anti-mouse IgG raised in goat) second antibody. The O.D. values were measured at 405 nm within 2 hours.

Examination for Antibodies Synthesized in vitro by LPMCs

Patients. Forty-eight patients undergoing colonic resection (n=30) or colonoscopy (n=18) at the Division of Gastroenterology, Universita La Spienza, Rome, Italy, were included for these studies. There were 19 patients with ulcerative colitis (12 male and 7 female; mean age±SEM 51±2 years; range 21-65), 10 symptomatic and 9 asymptomatic at the time of the study. Of these 19 ulcerative colitis patients, 13 underwent routine colonoscopy while 6 underwent colon resection. Indication for surgery in these 6 patients was steroid-dependence in 4/6, diffuse polyposis in 1/6 and no response to medical treatment in 1/6. The colitis was left-sided in 14 patients and extensive in 5 patients. At the time of the study, 10 of the 19 ulcerative colitis patients were taking oral steroids, 7 patients were on mesalamine medications (orally in 2 patients, rectally in 5), and 2 patients were not receiving any treatment. Twelve of the 19 patients were clinically and endoscopically active and 7 were in remission. The mean (±SEM) duration of the disease in patients with ulcerative colitis was 11±2 years (range 1-31 years). Twelve patients had colonic Crohn's colitis (7 males and 5 females; mean age±SEM 42±3 years; range 22-62 years). In the Crohn's colitis group, there were 6 symptomatic and 6 asymptomatic patients. Four of these 12 Crohn's colitis patients underwent routine colonoscopy, while 8 underwent surgery. Indication for surgery was steroid-dependence in 4, no response to medical treatment in 2 and abdominal abscess in 2. Five patients were taking steroids, and 7 were treated with oral mesalamine. The mean duration of the disease (±SEM) was 9±2 years (range, 1-17 years). The non-inflammatory bowel disease group included 1 patient with diverticular disease who underwent colonoscopy and 16 patients with colonic carcinoma who underwent colon resection. Among them, 11 were male and 6 females with mean age(±SEM) 58±3 years; range 34-72 years. In all subjects, the diagnosis was made according to the usual clinical, endoscopical, radiological and histological criteria. Patients with indeterminate colitis are not included in this study. Disease activity was assessed in patients with ulcerative colitis by the clinical history and endoscopy findings (19) and in patients with Crohn's colitis by the CDAI (20).

Tissue samples. Colonic mucosal specimens for isolation of LPMCs were taken from each disease group, immediately following colonic resection (total n=30: ulcerative colitis n=6, Crohn's colitis n=8, non-inflammatory bowel disease n=16). In case of colonoscopy, 4-5 biopsy specimens were obtained during the procedure from 18 subjects with ulcerative colitis (n=13), Crohn's colitis (n=4), and non-inflammatory bowel disease (n=1). Surgical and colonoscopic biopsy specimens were obtained from the distal 20 cm of the colon (ulcerative colitis: n=12; Crohn's colitis: n=7; non-inflammatory bowel disease: n=10), and from the area proximal to the sigmoid colon (ulcerative colitis: n=7; Crohn's colitis: n=5; non-inflammatory bowel disease: n=9).

Blood samples. Venous blood samples were obtained from each patient during the visit for colonoscopy or prior to surgery, sera separated and stored at −70° C.

Isolation of LPMCs from surgical specimens. Intestinal mucosa was dissected from surgical specimens within 1 hour of resection. LPMCs were isolated from surgical specimens using the Bull and Bookman enzymatic methods (21) with minor modifications, as described by Pallone et al (22). LPMCs were washed, counted, and the viability assessed by 0.1% Trypan blue exclusion. Contamination by epithelial cells of the LPMCs suspensions ranged between 10% and 16%, as shown by us and others (23-25). LPMC yield ranged from $2.5 \times 10^6$ to $11.5 \times 10^6$ LPMCs/g wet tissue. The viability of LPMCs ranged from 85% to 90% before cultures and from 50% to 70% on the 10th day of culture.

Isolation of LPMCs from Biopsy Specimens. LPMCs were isolated using the EDTA-collagenase as mentioned above with modifications for small samples (23,26,27). LPMC preparations obtained from biopsy specimens were comparable to surgical specimens in terms of yield and epithelial cells contamination, ranging from 0.9 to $4 \times 10^6$ from 4-5 biopsy specimens. The viability of LPMCs ranged from 85%-95% before culture to 50-70% on the 10th day.

LPMC cultures. Cells were resuspended in a complete medium ($2 \times 10^6$ per 2 ml) placed in 2.8 ml wells tissue culture plates (Falcon Plastic, franklin Lakes, N.J.), and cultured unstimulated at 37° C. in 5% CO2. Previous studies by us (23) and others (28,29) consistently demonstrated that "in vitro" pokeweed mitogen (PWM) stimulation does not increase the total and antigen-specific IgG antibodies release by LPMC, suggesting that LPMCs are already maximally stimulated "in vivo" by luminal antigens permeating the intestinal mucosa. In the present study, we, therefore, used limited paired cultures of LPMC with and without PWM (ulcerative colitis n=4; Crohn's colitis n=6; non-inflammatory bowel disease n=8). PWM was added with 1 ug/well (Gibco laboratories, Grand Island, N.Y.). On the 10th day, cells were harvested, counted and checked for viability and supernatants were collected, frozen within 1 hour, and stored at −20° C. until tested.

Estimation of IgG and IgG Subclass Specific Antibodies Against hTMs in Culture Supernatants and Sera Total IgG in culture supernatants were tested by ELISA as previously described (22,23). For anti-hTMs IgG reactivities, ELISA plates (Falcon Plastic) were separately coated with the four recombinant human tropomyosin isoforms (hTM1, hTM2, hTM3, hTM5) at 150 ng/well diluted in the carbonate buffer (pH 9.6) (100 ul/well). Purified recombinant hTM4 was not available for testing. As blank, additional wells were coated with BSA (0.5 ug/100 ul). After an overnight incubation at 4° C., plates were washed as above in PBS and 0.05% Tween 20 (200 ul/well). Non specific binding was blocked with 0.25% BSA in PBS (100 ul/well)

for 30 minutes at 37° C. After three washings, diluted supernatants (1:1) or sera (1:100) were added in triplicates (100 ul/well). Plates were incubated for 2 hours at 25° C. and then overnight at 4° C. After three washings, the alkaline-phosphatase-conjugated goat anti-human IgG (100 ul at 1:6000) (Sigma Chemical Co.) was added for the measurement of IgG antibodies to tropomyosins. For the IgG subclass analysis, alkaline phosphatase labeled anti-human IgG1, IgG2 and IgG3 were used (Zymed, San Francisco, Calif.) at 1:6000 (100 ml). After 1 hour at 25° C. and three washings, the substrate p-nitrophenyl-phosphate-disodium was added (100 ul) (5 ug/ml). After 1 hour at 25° C., plates were read at 405 nm. Results for each sample were expressed as the mean Optical Density (OD)±SD of triplicate values with the blank value against BSA subtracted from each value.

Statistical Analysis

ELISA results from both total and tropomyosin-specific IgG antibodies were not normally distributed in all groups. Therefore, the nonparametrical Mann-Whitney U Test was used for the statistical analysis of the data among groups and results expressed as mean±standard error of mean (SE) both in the text and tables.

Results

Figure 2:
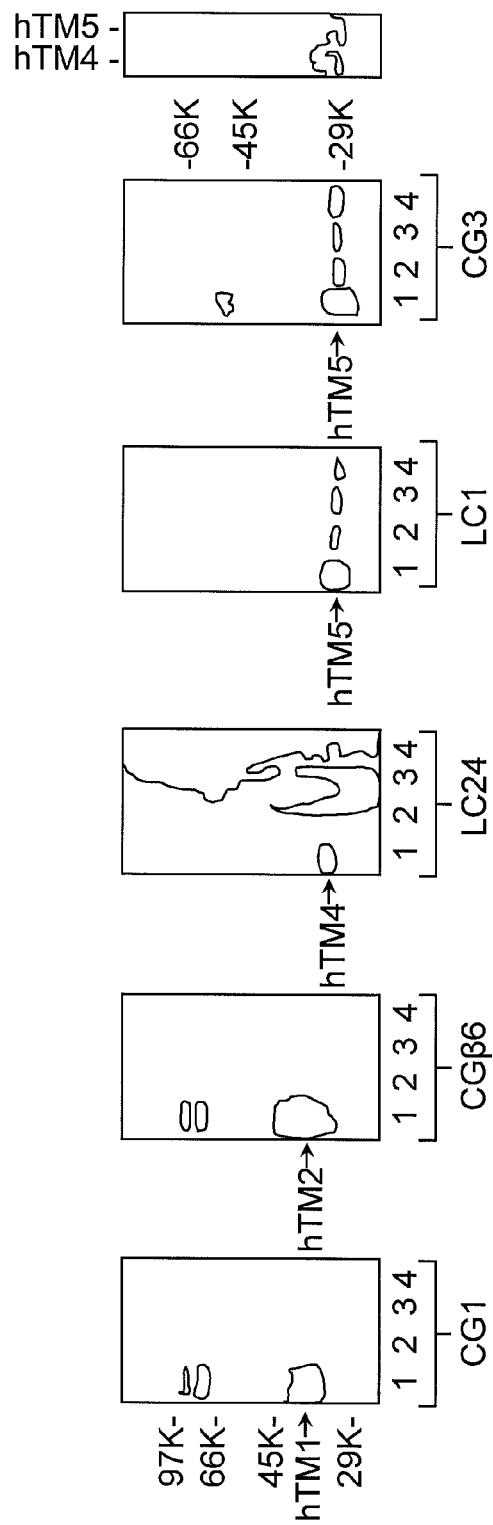
FIG. 2 illustrates an immunotransblot analysis of the enriched TM extracts from colon and jejunal epithelial cells using isoform specific monoclonal antibodies, CG1 (anti-hTM1), CGb6 (anti-hTM 2&3), LC24 (anti-hTM4), LC1 (anti-hTM5) and CG3 (anti-hTM5).

FIG. 1 demonstrates SDS-PAGE analysis followed by Coomassie blue staining of the recombinant hTM isoforms (hTM1, 2, 3, 4 & 5 in lanes 2-6 respectively) and enriched tropomyosins from colon smooth muscle (lane 7) (Mr 38K to Mr 40K) and colon epithelial cells (lane 8) (Mr 30K to Mr 32K). Recombinant hTM isoforms were synthesized by us from the respective cDNA clones (hTM1, 2, 3 & 5), expressed in the bacterial system and purified. A small amount of recombinant hTM4 was available and this was used as a reference sample to examine the specificity of the isoform specific anti-hTM monoclonal antibodies. The homogeneity of each of the purified hTM isoforms can be seen. The molecular weights of various isoforms varied from Mr 30K to Mr 40K. As shown in FIG. 2, using isoform specific anti-tropomyosin murine monoclonal antibodies, the specificity of various hTM isoforms is demonstrated by transblot analysis. The immunoreactivity was also tested by an ELISA. Each of the hTM isoform was examined using all of the monoclonal antibodies to determine the presence or absence of any cross reactivity. Isoform specificity of the hTMs and monoclonal antibodies were clearly evident. While CG1 mAb (IgG1 subclass) reacted exclusively with hTM1, LC-24 mAb (IgG1 subclass) reacted with hTM4 only. LC1 (IgG1 subclass) and CG3 (IgM isotype) monoclonal antibodies both reacted solely with hTM5. These 2 mAbs react with 2 different epitopes of hTM5 at a.a. residues 1-18 and 29-44 respectively (15,18). CGb6 mAb (IgM isotype) reacted with both hTM2 and hTM3. At this time, we do not have a mAb to differentiate between hTM2 and hTM3. As also shown in FIG. 1, colonic smooth muscle mainly contained high Mr TM isoforms (lane 7), whereas colonic epithelial cells contained low Mr TM isoforms (lane 8).

Figure 3:
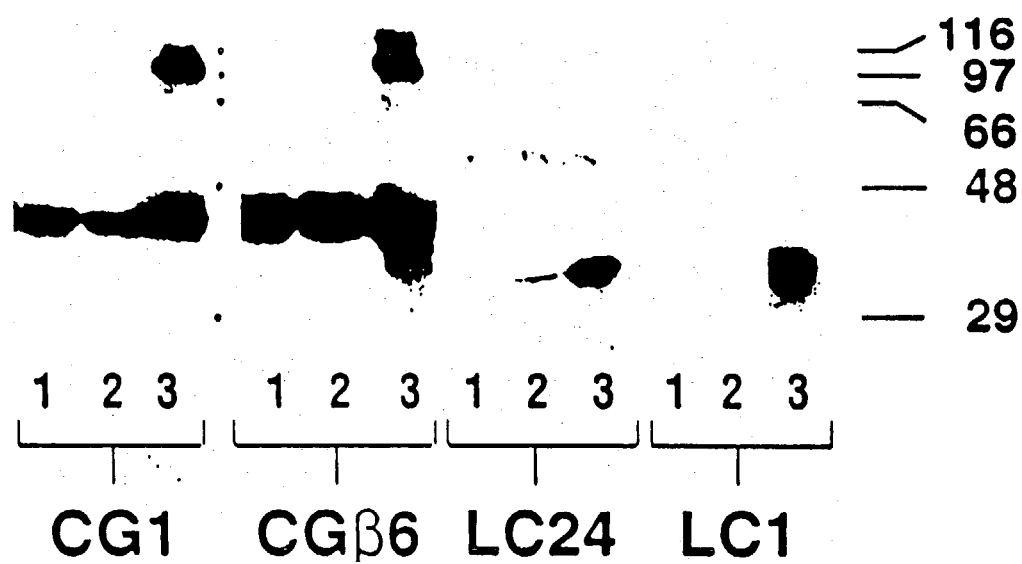
FIG. 3 illustrates an immunotransblot analysis of enriched TM preparations from the smooth muscle of intestine probed with the hTM isoform specific monoclonal antibodies against hTM1-5.

Western blot analysis of tropomyosins extracted from normal colonic and jejunal epithelial cells and intestinal smooth muscle are shown in FIGS. 2 and 3. The predominant hTM isoforms in normal colonic and jejunal epithelium are hTM5 and hTM4 which are lower Mr isoforms (Mr 30K-Mr 32K)compared to hTM1-3 (Mr 36K-Mr 40K) (FIGS. 1 and 2). Epithelial extracts did not contain any detectable amount of hTM1,2&3 (FIG. 2). In contrast, intestinal smooth muscles from both colon and jejunum contained predominantly higher hTM isoforms i.e. hTM1, 2 & 3 isoforms (FIG. 3). In the smooth muscle there was also a trace of hTM4 but no detectable amount of hTM5. Colonic and jejunal mucosal extracts contributed by epithelial and non-epithelial mucosal tissue, including muscularis mucosa, contained all the 5 isoforms as can be expected (data not shown).

Total IgG in LPMC Supernatants from Ulcerative Colitis in Comparison with Crohn's Colitis and Non-Inflammatory Bowel Disease Controls Total IgG levels (ng/ml) were higher in LPMC supernatants from patients with ulcerative colitis (452±155), and Crohn's colitis (404±147) when compared with non-inflammatory bowel disease (127±29) (p=0.04). Total IgG released by LPMC from ulcerative colitis and Crohn's colitis did not differ significantly. LPMCs from patients with symptomatic ulcerative colitis spontaneously released higher levels of total IgG (870±243) ng/ml than LPMCs from ulcerative colitis in remission (93±31) ng/ml (p=0.03), Crohn's colitis in remission (p=0.04) and non-inflammatory bowel disease (p=0.003). Levels of total IgG were also higher in LPMC supernatants from symptomatic Crohn's colitis (670±219) ng/ml than Crohn's colitis in remission (86±33) ng/ml (p=0.04), ulcerative colitis in remission (p=0.04) and non-inflammatory bowel disease (p=0.002). There were no significant differences in terms of total IgG release, between LPMCs isolated from biopsy specimens and surgical specimens from the inflammatory bowel disease patients and non-inflammatory bowel disease controls.

In inflammatory bowel disease patients, total IgG levels in LPMC supernatants did not significantly differ also in relation to steroid treatment, disease duration or age. As expected, PWM-stimulation did not significantly increase the release of total IgG by LPMCs from all groups (data not shown).

Figure 4:
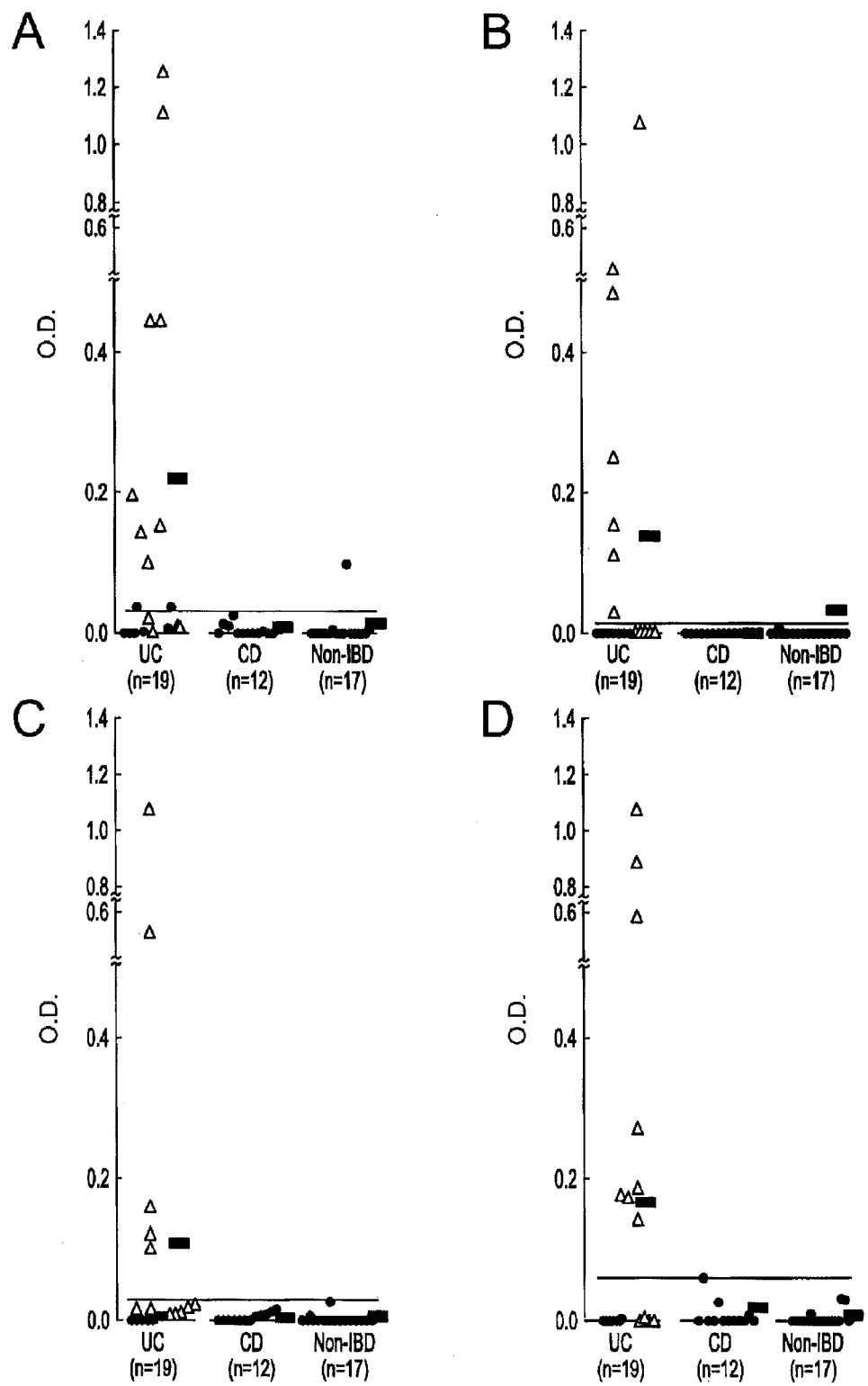
FIG. 4 illustrate a scatterogram showing the immunoreactivity of spontaneously produced IgG by LPMCs against hTM1,2,3 and 5.

IgG Antibodies Against Different hTM Isoforms Present in LPMC Supernatants from Ulcerative Colitis in Comparison with Crohn's Colitis and Non-Inflammatory Bowel Disease Controls In the ELISA, using the supernatants from cultured LPMCs against the four hTM isoforms (hTM 1, 2, 3 & 5), the OD values are shown for each of the 48 patients in the scatterogram (FIG. 4). The thick horizontal bar indicates the mean value for each patients' group against the hTM isoforms. The immunoreactivity of LPMC supernatants from ulcerative colitis against hTM1 and hTM5 was significantly higher when compared to LPMC supernatants from both Crohn's colitis and non-inflammatory bowel disease (hTM1: p=0.006 and p=0.001; hTM5: p=0.04 and p=0.01 respectively). However, the reactivity against hTM1 and hTM5 did not differ between Crohn's colitis and non-inflammatory bowel disease controls. Differently from hTM1 and hTM5, the mean OD values for IgG antibodies against hTM2 and hTM3 in LPMC supernatants. did not significantly differ among total group of ulcerative colitis, Crohn's colitis and non-inflammatory bowel disease controls.

The supernatants from cultured LPMC from 12 of 19 ulcerative colitis patients (63%) had clearly higher anti-TM reactivity against one or multiple hTM isoforms when compared to the mean plus three standard deviation value for Crohn's colitis (shown in FIG. 4 by the long horizontal line for each of the four hTM isoforms). These 12 patients included all 10 patients who were symptomatic both clinically and endoscopically, and 2 patients who were in clinical remission. Six of the 10 symptomatic patients had reactivity against both hTM1 & hTM5 isoforms. Four additional patients (two symptomatic and two in remission) showed high immunoreactivity against hTM1 but not hTM5 and two other patients (both symptomatic) showed reactivity against hTM5 and not against hTM1. Five of these six patients' sera (3/4 in the hTM1 group and 2/2 in the hTM5 group) were also tested against hTM 1 and hTM5. Four of the five sera (two in each group) showed parallel anti-hTM reactivity, whereas one serum did not react with either of the two hTM isoforms. The two sera in the hTM1 group reacted with both hTM1 and hTM5.

Although not statistically significant as a whole group of ulcerative colitis, the LPMC supernatants from 7 of the 12 ulcerative colitis patients who were reactive against hTM1 and/or hTM5 also showed higher reactivity against hTM2 and 5 of these 7 against hTM3 as well (FIG. 4), and all of them were symptomatic. However, none of the 12 patients with Crohn's colitis (6 active and 6 in remission) had values beyond the cutoff line of mean±3SD for Crohn's colitis. Only one of the 17 patients in the non-inflammatory bowel disease control group had high OD value against hTM1, 2 and 3, but not against hTM5 (FIG. 4). In general, LPMCs from the symptomatic ulcerative colitis group produced higher IgG antibodies to hTM1 and hTM5 (mean OD±SE: 0.386±0.162 & 0.337±0.140 respectively) than LPMCs from ulcerative colitis in remission (mean OD±SE: 0.049±0.019, 0.051±0.025 respectively) (p=0.04), symptomatic Crohn's colitis (mean OD±SE: 0.007±0.005 and 0.016±0.009 respectively) (p=0.03) and non-inflammatory bowel disease (mean OD±SE: 0.006±0.002 and 0.003±0.002 respectively) (p=0.002). The OD values for the IgG antibodies against any of the four hTM isoforms did not differ between patients with Crohn's colitis symptomatic or in remission and the non-inflammatory bowel disease controls.

The higher IgG immunoreactivity against hTM1 and hTM5 by LPMC supernatants in ulcerative colitis was not related to higher levels of total IgG levels in the same samples. Indeed, the total IgG for ulcerative colitis+ve vs ulcerative colitis−ve for hTM1 was 351±249 vs 538±206 ng/ml respectively and for hTM5, the total IgG was 466±329 vs 445±184 ng/ml; (p=not significant for both). PWM-stimulation did not significantly increase the release of hTM-specific IgG antibodies from LPMCs (data not shown). Within each disease group, levels of total and hTM-specific IgG did not significantly differ in supernatants from LPMC isolated from biopsy or surgical specimens, and between LPMC isolated from the distal 20 cm of the colon or from the descending colon proximal to 20 cm. Levels of total and hTM-specific IgG antibodies produced by LPMC from ulcerative colitis did not also differ in relation to clinical variables such as age, sex, duration of disease and therapy.

IgG Subclass Antibodies Against hTM1 and hTM5 Isoforms in Culture Supernatants and Sera from Ulcerative Colitis in Comparison with Crohn's Colitis and Non-Inflammatory Bowel Disease Controls As shown in Table 1, the major IgG reactivities of LPMC supernatants from patients with ulcerative colitis against hTM1 and hTM5 belong to IgG1 subclass. Antibodies against hTM1 and hTM5 belonging to IgG2 and IgG3 subclasses were almost undetectable in the LPMC supernatants. The IgG1 reactivities of the LPMC supernatants from ulcerative colitis against hTM1 and hTM5 were significantly (p=0.02 to 0.04) higher when compared to Crohn's colitis and non-inflammatory bowel disease controls (Table 1). The IgG1 reactivities against hTM1 and hTM5 for the ulcerative colitis sera were also significantly (p=0.01 to 0.04) higher when compared to sera from Crohn's colitis and controls. In addition, unlike mucosal IgG subclass antibodies against hTM1 and hTM5, ulcerative colitis sera also contained IgG2 subclass antibodies against hTM1 and hTM5. This reactivity was significantly (p=0.01 to 0.04) higher in ulcerative colitis when compared to Crohn's colitis and non-inflammatory bowel disease controls (Table 1). Such a difference was not observed in ulcerative colitis sera for the IgG3 reactivity against hTM1 or hTM5. There was no difference in the anti-hTM1 and anti-hTM5 reactivities in Crohn's colitis sera when compared to non-inflammatory bowel disease controls (Table 1).

TABLE 1.

Levels of IgG subclass antibodies (IgG1, IgG2, and IgG3) against hTM1 and hTM5 isoforms in the supernatants from cultured mucosal lymphocytes (LPMC) and sera from patients with UC, CD and non-IBD

| Patients | Antibodies against hTM1 and hTM5 isoforms (Mean OD ± SE) | | | |
|---|---|---|---|---|
| | hTM1 | | hTM5 | |
| | LPMC | Sera | LPMC | Sera |
| UC | | | | |
| IgG1 | 0.146 ± 0.100[a] | 0.248 ± 0.021[b] | 0.208 ± 0.026[c] | 0.691 ± 0.077[d] |
| IgG2 | 0.003 ± 0.001 | 0.108 ± 0.013[e] | 0.014 ± 0.009 | 0.218 ± 0.042[f] |
| IgG3 | 0.010 ± 0.005 | 0.007 ± 0.004 | 0.012 ± 0.008 | 0.004 ± 0.002 |
| CD | | | | |
| IgG1 | 0.116 ± 0.007 | 0.152 ± 0.032 | 0.133 ± 0.010 | 0.420 ± 0.111 |
| IgG2 | 0.001 ± 0.002 | 0.010 ± 0.002 | 0.003 ± 0.006 | 0.058 ± 0.028 |
| IgG3 | 0.005 ± 0.002 | 0.002 ± 0.003 | 0.003 ± 0.003 | 0.002 ± 0.003 |
| Non-IBD | | | | |
| IgG1 | 0.113 ± 0.007 | 0.102 ± 0.008 | 0.135 ± 0.007 | 0.363 ± 0.080 |
| IgG2 | 0.003 ± 0.003 | 0.003 ± 0.002 | 0.001 ± 0.003 | 0.063 ± 0.018 |
| IgG3 | 0.003 ± 0.002 | 0.004 ± 0.002 | 0.002 ± 0.006 | 0.002 ± 0.003 |

LPMC:
[a] p = 0.02 UC vs CD and p = 0.03 UC vs non-IBD
[c] p = 0.04 UC vs CD and non-IBD
Sera:
[b] p = 0.01 UC vs CD and p = 0.03 UC vs non-IBD
[d] p = 0.04 UC vs CD and non-IBD
[e] p = 0.03 UC vs CD and p = 0.01 UC vs Non-IBD
[f] p = 0.04 UC vs CD and non-IBD FIG. 1. SDS-Polyacrylamide gel electrophoresis followed by Coomassie blue staining of purified recombinant human tropomyosin isoforms (hTM1-5) and enriched hTMs from colon epithelial cells and colon smooth muscle. Lanes 2 to 6 contain hTM1-5 respectively. The molecular weights of various hTM isoforms vary from Mr 30K to Mr 40K. Lane 7 contains enriched TM preparation from smooth muscle of colon and lane 8 contains enriched TM preparation from colon epithelial cells. The colon epithelial cells contain low Mr hTMs (Mr 30K to Mr 32K) whereas smooth muscle contain mostly high Mr hTMs (Mr 38K to Mr 40K).

FIG. 2. Immunotransblot analysis of the enriched TM extracts from colon and jejunal epithelial cells using isoform specific monoclonal antibodies, CG1 (anti-hTM1), CGb6

(anti-hTM 2&3), LC24 (anti-hTM4), LC1 (anti-hTM5) and CG3 (anti-hTM5). Lanes 1 in each panel contain respective recombinant hTM isoforms. For CGb6 hTM2 was used. Lanes 2 and 3 in each panel contain enriched TM preparations from 2 different specimens of colon epithelial cells and lanes 4 contain enriched TM from a jejunal epithelial cells. Both colonic and jejunal epithelial cells contain hTM5 and hTM4, and there was no detectable hTM1,2 or 3. The two extreme right lanes show recombinant hTM4 and hTM5 (Mr ~30K) separated by SDS-polyacrylamide gel electrophoresis and stained with Coomassie blue.

FIG. 3. Immunotransblot analysis of enriched TM preparations from the smooth muscle of intestine probed with the hTM isoform specific monoclonal antibodies against hTM1-5. Lanes 3 in each panel contain respective recombinant hTM isoforms. Lanes 1 contain enriched TM extract from colonic smooth muscle and lanes 2 contain similar preparation from jejunal smooth muscle. Both colonic and jejunal smooth muscle contain mainly hTM1, hTM2 and/or hTM3 and a trace of hTM4. There was no detectable hTM5.

FIG. 4. Scatterogram showing the immunoreactivity of spontaneously produced IgG by LPMCs against hTM1,2,3 and 5. The individual OD value for each of the LPMC-supernatant from the 48 patients with UC (n=19), CD (n=12), and non-IBD controls (n=17) is shown here. In the UC group, there were 12 symptomatic patients (identified by a D) and 7 patients were in remission (closed circle, f). Of the 12 CD patients with colonic disease, 6 were active and 6 were in remission. The continuous horizontal line shown for each hTM isoform represents the mean value plus three standard deviations for the CD group against the respective hTM isoforms. The short, thick horizontal bar indicates the mean value for the group.

DISCUSSION

The results from this study demonstrate that normal human intestine contains several isoforms of tropomyosins and there are clear differences between epithelium and smooth muscle. Epithelial cells from both colon and jejunum contain mainly hTM5 followed by hTM4, whereas smooth muscle contain hTM1, hTM2 and 3. Since the monoclonal antibody CGb6 does not differentiate between hTM2 and hTM3, at present we do not know whether intestinal smooth muscle contains either or both of these 2 hTM isoforms. Since the mucosa contains both epithelium and muscularis propria and other cells, total mucosal tropomyosin preparation included all of the 5 isoforms. Indeed, these findings explain our earlier report demonstrating multiple tropomyosin related bands in the colonic mucosal extracts (23).

Tropomyosins can induce significant autoimmune responses (17). Physicochemical and biochemical analyses of 109 human autoantigens demonstrated that sequences longer than 27 residues with coiled-coil alpha-helices are the forerunner autoantigens for various human autoimmune diseases and several sequences of tropomyosin residues were considered to be the most potent autoantigens (17). Tropomyosin has also been found to be the major allergen related to seafood and house dust mite (16,30), and about 80% of shrimp-allergic subjects contain IgE and IgG serum antibody reactive with a 36KD tropomyosin extracted from shrimp (16).

Multicellular organisms exhibit multiplicity of tropomyosin isoforms. For example, at least 12 isoforms have been identified in rat on the basis of primary sequence differences with molecular weights ranging from Mr 30K to 40K (14).

At least 8 distinct isoforms of tropomyosins are isolated from human fibroblast (15) and organ specific isoforms have been well characterized (14). Four genes are identified in human and various isoforms are synthesized by alternate RNA splicing mechanism restricted to three exon regions (14, 32-33). Each tropomyosin molecule is a rod-shaped coiled-coil dimeric protein associated with the actin filaments, caldesmone, and tropomodulin and involved in cell shape, cytokinesis, intracellular granule movement (14,33), and other functions such as maintenance of cellular polarity in developing tissue (34). While by and large tropomyosins are intracellular proteins, they have also been found in the cell membrane e.g. in erythrocytes (35), including at the root of the brush border of the small intestine (36). Independent protein with partial (35%) homology to tropomyosin has also been isolated from the brush border of the small intestine (37).

Several independent studies recently demonstrated IgG autoantibody responses against tropomyosins in ulcerative colitis but not in Crohn's colitis (13,38,39). Using a large number of inflammatory bowel disease patients and their first degree blood relatives, one study from Italy reported that sera from about two-thirds of these Italian patients with ulcerative colitis contained autoantibody against hTM-5 and about half of the patients against hTM-1 (38). Twenty percent of these patients' healthy first-degree relatives were found to have autoantibody against hTM-1 only. In contrast, patients with Crohn's colitis and their healthy relatives did not have such antibody response (p<0.001) (38). Another study from Japan also reported the presence of anti-tropomyosin antibody in the circulation of patients with symptomatic ulcerative colitis (39), although hTM isotype was not analyzed. Furthermore, these investigators reported that tryptic peptide(s) of tropomyosin bind with specific class II molecule (HLA-DPw9) and is expressed on the surface of L cells transfected with class II genes, and the serum from ulcerative colitis contains autoantibody that recognizes the tropomyosin-peptide on the surface of transfected L cells (39). In one study from the United Kingdom, anti-tropomyosin antibodies were not demonstrated in ulcerative colitis (40). In this study, from colonic mucosa, 2 tropomyosin related proteins of 37 kDa and 39 kDa, which co-migrated in SDS-polyacrylamide gel electrophoresis with porcine tropomyosin, were electroeluted and used in an ELISA as antigen. No reactivity was seen with any of the human sera, including ulcerative colitis, Crohn's colitis, non-inflammatory bowel disease controls. This complete non-reactivity can be explained due to the loss of antigenicity by SDS-treatment which is a common phenomenon with autoantibodies (41). Using colonic mucosal extract enriched in tropomyosins, we earlier reported non-reactivity of autoantibodies in ulcerative colitis by immunotransblot analysis, although the reactivity was evident in the ELISA using the same extract prepared without SDS treatment (23).

Recently, IgG antibodies against tropomyosin have been demonstrated in an animal model of $TCR^{-/-}$ mice who develop spontaneous colitis. Interestingly, there was a positive correlation of anti-tropomyosin antibody titer with the severity of colitis (42). However, it is unknown whether the autoantibody response in this mouse model of colitis is directed against any of the known hTM isoforms. This group further demonstrated that autoantibody producing B cells directed against tropomyosin was increased in the appendix lymphoid follicle compared to Peyer's Patches, suggesting selectivity of the mucosal immune response against tropomyosin (43).

In this study, we have purified recombinant hTM isoforms and using the four hTM isoforms (hTM1-3 and hTM5), we have demonstrated that unstimulated LPMCs from the colon of 12 of 19 (63%) patients with ulcerative colitis synthesize IgG autoantibody in vitro that preferentially reacts against certain hTM isoforms, particularly hTM5 and hTM1. Ten of these 12 patients were symptomatic. Following antigenic stimulation by a tropomyosin-peptide(s), the autoreactive B cells may be polyclonal and may produce antibodies to different parts of the tropomyosin isoform which will show cross-reactivity to other hTM isoforms because of the shared areas among the isoforms. Indeed, five of the 12 symptomatic ulcerative colitis patients did show anti-tropomyosin activities to all the 4 hTM isoforms, while the others had more restricted antibody activity against hTM5 and/or hTM1. However, none of the Crohn's colitis patients showed any reactivity against any of the 4 hTM isoforms, although each of the 12 Crohn's colitis patients had colonic involvement, and 6 of these patients had active disease. This suggests that the autoantibody response is not a secondary effect of colonic inflammation. The absence of anti-tropomyosin autoantibody response in the remaining 7/19 ulcerative colitis patients who were mostly in remission may be due to insufficient in vitro synthesis of IgG by LPMCs for detection by the ELISA. The non-reactive group may also suggest a subgroup. Although we did not examine the purified hTM5 extracted from patient's own colonocytes and instead we used recombinant hTM5, it is expected that local autoantibody should react with the autologous hTM5. This is supported by our previous observation that colon-tissue bound IgG from ulcerative colitis recognized the tropomyosin related Mr 40K protein isolated from the autologous colon (9). In this study, we did not examine the pANCA status of the patients. However, the study from Italy (38) reported a significant ($p<0.04$) correlation of positive pANCA status with the presence of anti-hTM5 antibody in sera from patients with ulcerative colitis. The predominant hTM isoform present in the colon epithelium, as shown here, is hTM5, and autoantibody response against hTM5 is evident. hTM4 is also present in smaller amount in the epithelial cells. Recombinant hTM4 was not available and antibody response against hTM4 was not studied. It is interesting that a significant autoantibody response in ulcerative colitis was demonstrated against hTM1. This may suggest that the major autoantigenic epitope(s) may be located in the common region(s) between hTM5 and hTM1. The autoantibody response against hTM1 may also be due to an ectopic expression of hTM1 related epitope in ulcerative colitis colon epithelium which is currently unknown.

To understand a possible role of hTM5 or related protein in the pathogenesis of ulcerative colitis, one needs to explain that since hTM5 is present in both colonocytes and small intestinal enterocytes, why isn't there small bowel involvement in patients with ulcerative colitis? It is intriguing that we recently observed a selective expression of hTM5 on the surface of colon epithelial cells and not on small intestinal enterocytes (44). Of all the 5 hTM isoforms (hTM1-5), only hTM5 epitope was identified on the surface of normal colonic epithelial cells by FACS analysis and immunoelectronmicroscopy (44). Indeed, none of the monoclonal antibodies against hTM1, 2, 3 & 4, reacted with the freshly isolated normal colon epithelial cells; whereas CG3 monoclonal antibody (anti-hTM5) consistently reacted on colonocytes in the FACS analysis. In contrast to colonocytes, small intestinal (both jejunum and ileum) epithelial cells, however, did not react with any of the monoclonal antibodies, including CG3. This raises the possibility that hTM5 related epitope expressed on the surface of colon epithelial cells may be involved in stimulating the effector immune system as well as a target for immune attack restricted to the colon. Such an organ-specific antigenic display may play an important role for a local trigger of immune response and perpetuation of the disease in the colon and not in the small intestine. Indeed, recently antigenic display of myosin has been found to be involved in the pathogenesis of autoimmune myocarditis (45), which may also be genetically determined (46). Molecular mimicry, related to a specific peptide in streptococcal M protein and tropomyosin, has been found to be an important pathogenetic factor in autoimmune myocarditis (47). Such a molecular mimicry against bacterial product (48) may influence the mucosal immune functions and be responsible for perpetuation and flare-up of the disease.

While IgG autoantibody response against tropomyosin in ulcerative colitis has been demonstrated by the 3 groups of investigators (13,38,39), T-cell response to tropomyosins in ulcerative colitis is unknown. Physicochemically, tropomyosin-peptide(s) could be strong potential autoantigen(s) (17). The knowledge of normal colon epithelial specific hTM isoforms and the autoantibody response against hTMs in ulcerative colitis, will facilitate future studies to focus on the identification of the hTM peptide(s) capable of cellular and humoral immune responses in patients with ulcerative colitis. Such investigation should provide important biochemical information to explain autoimmune mechanism in ulcerative colitis and may help to develop strategies for possible immune therapy.

The antibodies of the present invention may be used together with pharmaceutically acceptable carriers to provide pharmaceutical compositions which can be administered to a human orally or rectally, or both, in amounts effective to provide a variety of therapeutic activity. Of course, the type of carrier will vary depending upon the mode of administration desired for the pharmaceutical composition as is conventional in the art. Preferably, the antibody is administered orally or rectally to the human.

It is especially advantageous to formulate the pharmaceutical compositions in dosage unit forms for ease of administration and uniformity of dosage. The term dosage unit forms as used herein refers to physically discrete units suitable for use as a unitary dosage, each unit containing a predetermined quantity of active ingredient calculated to produce the desired therapeutic effect in association with the pharmaceutical carrier.

REFERENCES

1. Brandtzaeg P. Autoimmunity and ulcerative colitis: can two enigmas make sense together? Gastroenterology 1995; 109:307-312.

2. Baklien K, Brandtzaeg P. Comparative mapping of the local distribution of immunoglobulin-forming cells in ulcerative colitis and Crohn's disease of the colon. Clin Exp Immunol 1975;22:197-209.

3. Hibi T, Ohara M, Toda K, Hara A, Ogata H, Iwao Y, Watanabe N, Watanabe M, Hamada Y, Kobayashi K, Aiso S, Tsuchiya M. In vitro anticolon antibody production by mucosal or peripheral blood lymphocytes from patients with ulcerative colitis. Gut 1990;31:1371-1376.

4. Targan S R, Landers C J, Cobb L, MacDermott R P, Vidrich A. Perinuclear anti-neutrophil cytoplasmic antibodies are spontaneously produced by mucosal B cells in ulcerative colitis patients. J Immunol 1995;155:3262-3267.

5. Scott M G, Nahm M H, Macke K, Nash G S, Bertovich M J, MacDermott R P. Spontaneous secretion of IgG subclasses by intestinal mononuclear cells; differences between ulcerative colitis, Crohn's disease and controls. Clin Exp Immunol 1986;66:209-215.

6. Brandtzaeg P, Halstensen T, Kett K. Immunopathology of inflammatory bowel disease. In: MacDermott R P, and Stenson W F, eds. Inflammatory Bowel Disease. New York: Elsevier, 1992:95-136.

7. Heiner D C. Significance of immunoglobulin G subclasses. Am J Med 1984;76:1-6.

8. Das K M, Dubin R, Nagai T. Isolation and characterization of colonic tissue-bound antibodies from patients with idiopathic ulcerative colitis. Proc Natl Acad Sci USA 1978; 74:4528-4532.

9. Takahashi F, Das K M. Isolation and characterization of a colonic autoantigen specifically recognized by colon tissue-bound IgG from idiopathic ulcerative colitis. J Clin Invest 1985;76:311-318.

10. Halstensen T S, Mollnes T E, Garred P, Fausa O, Brandtzaeg P. Epithelial deposition of immunoglobulin G1 and activated complement (C3b and terminal complement complex) in ulcerative colitis. Gastroenterology 1990;98:1264-1271.

11. Halstensen T S, Das K M, Brandtzaeg P. Epithelial deposits of immunoglobulin G1 and activated complement co-localize with the 40 kDa colonic autoantigen in ulcerative colitis. Gut 1993;34:650-657.

12. Halstensen T S, Mollnes T E, Garred P, Gausa O, Brandtzaeg P. Surface epithelium-related activation of complement differs in Crohn's disease and ulcerative colitis. Gut 1992;33:902-908.=

13. Das K M, Dasgupta A, Mandal A. Autoimmunity to cytoskeletal protein tropomyosin(s): a new clue to the pathogenetic mechanism for ulcerative colitis. J Immunol 1993; 150:2487.

14. Lin J J-C, Warren K S, Wamboldt D D. Tropomyosin isoforms in nonmuscle cells. International Review Cytology 1997;170:1-38.

15. Novy R E, Lin J L-C, Lin J J-C. Human fibroblast tropomyosin isoforms: characterization of cDNA clones and analysis of tropomyosin isoform expression in human tissues and in normal and transformed cells. Cell Motil Cytoskeleton 1993;25:267-281.

16. Daul C B, Slattery M, Reese G, Lehrer S B. Identification of the major brown shrimp (penaeus aztecus) allergen as the muscle protein tropomyosin. Int Arch Allerg Immunol 1994;105:49-55.

17. Dohlman J G, Lupas A, Carson M. Long charge-rich alpha-helices in systemic autoantigens. Biochem and Biophys Research Communications 1993;195:686-696.

18. Novy, R E, Liu L F, Lin C-S, Helfman D M, Lin J J-C. Expression of smooth muscle and nonmuscle tropomyosin in E. coli and characterization of bacterially produced tropomyosins. Biochemica et Biophysica Acta 1993;1162:255-265.

19. Truelove S C, Witts L J. Cortisone in ulcerative colitis. Final report on a therapeutic trial. BMJ 1955;2:1041-1048.

20. Best W R, Becktel K M, Singleton J W, Kern F. Development of a Crohn's disease activity index. National cooperative Crohn's disease study. Gastroenterology 1976; 70:439-444.

21. Bull D M, Bookman M A. Isolation and functional characterization of human mucosal lymphoid cells. J Clin Invest 1977;59:966-974.

22. Pallone F, Fais S, Squarcia O, Biancone L, Pozzili P, Boirivant M. Activation of peripheral and intestinal lamina propria lymphocytes in Crohn's disease. In vivo state of activation and in vitro response to stimulation ad defined by the expression of early activation antigens. Gut 1987;28:745-753.

23. Biancone L, Mandal A, Yang H, Dasgupta T, Paoluzi A O, Marcheggiano A, Paoluzi P, Pallone F, Das K M. Production of immunoglobulin G and G1 antibodies to cytoskeletal protein by lamina propria cells in ulcerative colitis. Gastroenterology 1995;109:3-12.

24. Fiocchi C, Battisto J R, Farmer R G. Gut mucosal lymphocytes in inflammatory bowel disease. Isolation and preliminary functional characterization. Dig Dis Sci 1979; 24:705-717.

25. MacDermott R P, Nash G S, Nahm M H. Antibody secretion by intestinal mononuclear cells from normal controls and inflammatory bowel disease patients. Immunol Invest 1989;18:449-457.

26. Miyazaki H, Kawasaki H, Hirayama C. Studies on lymphocyte subpopulations in human biopsy specimens by colonoscopy. Dig Dis Sci 1985;30:143-148.

27. Squarcia O, Fais S, Boirivant M, DiPaolo M C, Marcheggiano A, Iannoni C, Paoluzi P, Pallone F. Phenotypes and spontaneous immunoglobulin production in mononuclear cells suspensions isolated from colonic biopsies of patients with mild active and quiescent ulcerative colitis. Gastroenterol Clin Biol 1991;15:194-198.

28. Goodacre R, Davidson R, Singal D, Bienenstock J. Morphologic and functional characteristics of human intestinal lymphoid cells isolated by a mechanical technique. Gastroenterology 1979;76:300-308.

29. MacDermott R P, Nash G S, Bertovich M J, Sedine M V, Bragdon M J, Beale M G. Alterations of IgM, IgG and IgA synthesis and secretion by peripheral blood and intestinal mononuclear cells from patients with ulcerative colitis and Crohn's disease. Gastroenterology 1981;81:844-852.

30. Aki T, Kodama T, Fujikawa A, Miura K, Shigeta S, Wada T, Jyo T, Murooka Y, Oka S, Ono K. Immunochemical characterization of recombinant and native tropomyosin as a new allergen from the house dust mite, Dermatophagoides farinae. J Allergy Clin Immunol 1995;96:74-83.

31. Goodwin L O, Lees-Miller J P, Leonard M A, Chaley S B, Helfman D M. Four fibroblast tropomyosin isoforms are expressed from the rat alpha-tropomyosin gene via alternative RNA splicing and the use of two promoters. J Biol Chem 1991;266:8408-8410.

32. Lees-Miller J P, Helfman D M. The molecular basis for tropomyosin isoform diversity. Bioessays 1991;13:429.

33. Burgess D R, Broschat K O, Hayden J M. Tropomyosin distinguishes between the two actin-binding sites of willin and affects actin-bindings properties of other brush border proteins. J Cell Biol 1987;104:29-31.

34. Sung L A, Lin J J-C. Erythrocyte tropomodulin binds the N-terminus of hTM5, a tropomyosin encoded by the Y-TM gene. Biochem Biophys Res Comm 1994;201:627-634.

35. Fowler V M, Bennett V. Erythrocyte membrane tropomyosin: purification and properties. J Biol Chem 1984; 259:5978-5989.

36. Mooseker M S. Organization, chemistry and assembly of the cytoskeletal apparatus of the intestinal brush border. Annu Rev Cell Biol 1985;1:209-211.

37. Bikle D D, Munson S, Morrison N, Eisman J. Zipper protein, a newly described tropomyosin-like protein of the intestinal brush border. J Biol Chem 1993;268:620-626.

38. Biancone L, Monteleone G, Pallone F. Serum IgG against specific tropomyosin (TM) isoform in ulcerative colitis patients and unaffected relatives. Gastroenterology 1996;110:A864.

39. Sakamaki S. Hayashi S, Takayanagi N, Niitsu Y. Autoantibodies in sera of patients with ulcerative colitis recognize tropomyosin peptide associated with HLA-DPw9. Gastroenterology 1996;110:A1007.

40. Khoo U Y, Bjarnason I, Donaghy A, Williams R, MacPherson A. Antibodies to colon epithelial cells from the serum and colonic mucosal washings in ulcerative colitis. Gut 1995;37:63-70.

41. Bini P, Gabay J E, Teitel A, Melchior M, Zhou J-L, Elkon K B. Antineutrophil cytoplasmic autoantibodies in Wegner's granulomatosis recognize conformational epitope (s) on proteinase 3'. J Immunol 1992;149:1409-1415.

42. Mizoguchi A, Mizoguchi E, Chiba C, Spiekermann G M, Tonegawa S, Nagler-Anderson C, Bhan A K. Cytokine imbalance and autoantibody production in T cell receptor-a mutant mice with inflammatory bowel disease. J Exp Med 1996;183:847-856.

43. Mizoguchi A, Mizoguchi E, Chiba C, Bhan A K. Role of appendix in the development of inflammatory bowel diseases in TCR-a mutant mice. J Exp Med 1996;184:707-715.

44. Yoshizaki N, Kesari K, Lin J, Das K M. Expression of a tropomyosin-related protein on the surface of colon epithelial cells and its possible functional significance. Gastroenterology 1996;110:A1051.

45. Liao L, Sindhwani R, Rojkind M, Factor S, Leinwand L, Diamond B. Antibody-mediated autoimmune myocarditis depends on genetically determined target organ sensitivity. J Exp Med 1995;181:1123-1131.

46. New N, Rose N R, Beisel K W, Herskowitz A, Gurri-Glass G, Craig S W. Cardiac myosin induces myocarditis in genetically predisposed mice. J Immunol 1987; 139:3630-3636.

47. Fenderson P G, Fischetti V A, Cunningham M W. Tropomyosin shares immunologic epitopes with group A streptococcal M proteins. J Immunol 1989;142:2475-2480.

48. Sartor R B. Cytokines in intestinal inflammation: Pathophysiological and clinical considerations. Gastroenterology 1994;106:533-539.

Throughout this application, various publications have been referenced. The disclosures in these publications are incorporated herein by reference in order to more fully describe the state of the art.

While the invention has been particularly described in terms of specific embodiments, those skilled in the art will understand in view of the present disclosure that numerous variations and modifications upon the invention are now enabled, which variations and modifications are not to be regarded as a departure from the spirit and scope of the invention. Accordingly, the invention is to be broadly construed and limited only by the scope and spirit of the following claims.

I claim:

1. A method for treating ulcerative colitis in a human which comprises orally or rectally administering to the human a therapeutically effective amount of CG1, a murine IgG1 monoclonal antibody, which binds to tropomyosin isoform hTM1 associated with ulcerative colitis.

2. The method according to claim 1, wherein the antibody is administered in an amount from about 50 µg/day to about 500 µg/day.

3. The method according to claim 1, wherein the antibody is administered rectally.

* * * * *